United States Patent
Thalhammer (10) Patent No.: US 9,354,143 B2
(45) Date of Patent: May 31, 2016

(54) DEVICE AND METHOD FOR THE AUTOMATED ISOLATION AND TRANSFER OF AT LEAST ONE MICROSCOPIC SAMPLE FROM A SAMPLE CARRIER TO A COLLECTING SYSTEM

(75) Inventor: Stefan Thalhammer, Munich (DE)

(73) Assignee: HELMHOLTZ ZENTRUM MUNCHEN DEUTSCHES FORSCHUNGSZENTRUM FUR GESUNDHEIT UND UMWELT (GMBH), Neuherberg (DE)

( * ) Notice: Subject to any disclaimer, the term of this patent is extended or adjusted under 35 U.S.C. 154(b) by 513 days.

(21) Appl. No.: 13/819,907

(22) PCT Filed: Aug. 25, 2011

(86) PCT No.: PCT/EP2011/064591
§ 371 (c)(1),
(2), (4) Date: Feb. 28, 2013

(87) PCT Pub. No.: WO2012/028519
PCT Pub. Date: Mar. 8, 2012

(65) Prior Publication Data
US 2013/0171617 A1      Jul. 4, 2013

Related U.S. Application Data

(60) Provisional application No. 61/378,181, filed on Aug. 30, 2010.

(30) Foreign Application Priority Data

Aug. 30, 2010   (EP) .................................... 10174557

(51) Int. Cl.
*G01N 1/14*      (2006.01)
*G01N 1/28*      (2006.01)
(Continued)

(52) U.S. Cl.
CPC ................ *G01N 1/14* (2013.01); *C12Q 1/6806* (2013.01); *C12Q 3/00* (2013.01); *G01N 1/2813* (2013.01); *G01N 2001/282* (2013.01); *Y10T 436/25* (2015.01)

(58) Field of Classification Search
None
See application file for complete search history.

(56) References Cited

U.S. PATENT DOCUMENTS

2004/0252291 A1    12/2004  Schutze
2006/0139621 A1*   6/2006  Baer et al. ........................ 356/36
(Continued)

FOREIGN PATENT DOCUMENTS

CN        1865432 A    11/2006
EP        2 083 257 A1  7/2009
(Continued)

OTHER PUBLICATIONS

Japanese Office Action for Application No. 2013-525303, issued Jan. 20, 2015 (11 pages).
(Continued)

*Primary Examiner* — Robert R Raevis
(74) *Attorney, Agent, or Firm* — Nutter McClennen & Fish LLP; John J. Penny, Jr.

(57) ABSTRACT

A device for the automated isolation and transfer of at least one microscopic sample from a sample carrier to a collecting system for subsequent automatic analysis is provided. The device comprises a selection unit for selecting at least one sample located on the sample carrier, a controllable isolation unit for the automated isolation of the at least one selected sample, a controllable transfer unit, which has carrier means for the defined receiving and deposition of the at least one selected isolated sample, for an automated and defined transfer of the at least one selected isolated sample from the sample carrier to the collecting system, and a control unit, which has a data link to the selection unit, the isolation unit and the transfer unit, for an automated isolation and transfer operation.

28 Claims, 5 Drawing Sheets

(51) Int. Cl.
*C12Q 1/68* (2006.01)
*C12Q 3/00* (2006.01)

(56) References Cited

U.S. PATENT DOCUMENTS

2008/0072723 A1* 3/2008 Nakajima et al. ............... 83/102
2009/0045354 A1 2/2009 Sagmuller et al.
2012/0273692 A1* 11/2012 Tokuda et al. ................ 250/400

FOREIGN PATENT DOCUMENTS

| JP | 02-020278 A | 1/1990 |
|----|----|----|
| JP | 2003-161893 A | 6/2003 |
| JP | 2005-506546 A | 3/2005 |
| JP | 2006-064603 A | 8/2006 |
| JP | 2010-002213 A | 1/2010 |
| WO | 02/37159 A2 | 5/2002 |
| WO | 03/036266 A1 | 5/2003 |
| WO | 2009/092495 A1 | 7/2009 |

OTHER PUBLICATIONS

International Search Report mailed Oct. 6, 2011 for Application No. PCT/EP2011/064591 (6 Pages).
Chinese Office Action for Application No. 2011800418163, issued Jul. 21, 2014 (22 pages).

* cited by examiner

DEVICE AND METHOD FOR THE AUTOMATED ISOLATION AND TRANSFER OF AT LEAST ONE MICROSCOPIC SAMPLE FROM A SAMPLE CARRIER TO A COLLECTING SYSTEM

CROSS-REFERENCES TO RELATED APPLICATIONS

This application claims benefit of the U.S. Provisional Application No. 61/378,181, filed Aug. 30, 2010, and of the European patent application No. 10 174 557.8, filed Aug. 30, 2010, the entire disclosures of which are herein incorporated by way of reference. Moreover, the entire disclosure of the European patent application No. 08 150 662.8, filed Jan. 25, 2008, is incorporated herein by way of reference.

FIELD OF THE INVENTION

The present invention relates to a device and a method for the automated isolation and transfer of at least one microscopic sample from a sample carrier to a collecting system.

Although they are applicable to any samples, the present invention and the problems on which it is based are described in greater detail in the following, by way of example, in relation to membrane-supported samples, and in this context in particular in relation to membrane-supported microdissectates, in particular microdissectates which are isolated by means of laser-assisted microdissection.

BACKGROUND OF THE INVENTION

Laser-assisted microdissection makes it possible to isolate extremely small regions of a slice of tissue—which may comprise both fixed and living cell systems—down to individual cells. Moreover, with contactless laser manipulation, the microdissection of individual cell compartments can be ensured, for example cell organelles, chromosomes and chromosome fragments. Using a combination of PCR, cloning techniques and laser microdissection, it is possible to develop region-specific chromosomal samples for molecular cytogenetics. However, in these approaches based on laser microdissection, the fragments are collected using a glass needle which is made as fine as possible, in a manner comparable with glass needle microdissection. One development in laser microdissection resulted from the introduction of laser capture microdissection. In this method, a plastics material membrane is applied to the area which is to be analysed. The cells which are to be isolated are removed from the tissue thermally by locally fusing the film.

Laser pressure catapulting (LPC or LMPC) is an approach to isolating individual cells and cell groups which uses a different methodology. In this technique, a pulsed UV laser having power peaks of a few watts is directed onto the tissue region which is to be isolated. By contrast with laser capture microdissection, the tissue is applied to an ultra-fine carrier membrane, which has a thickness of a few μm. By means of a pulsed UV microlaser beam, cells or cell groups can be isolated in a targeted manner, and are isolated into a collecting device in a further operational step by means of a high-energy light pulse. Once the deposition has been verified optically, the isolated material is available for further biochemical methods.

Document WO 2005/107949 A1 discloses a method and a device for producing an analysis arrangement comprising discrete separate measurement regions for the purposes of biological, biochemical or chemical analysis.

SUMMARY OF THE INVENTION

In view of the aforementioned known approaches, one idea of the present invention is to provide a further improved device and an improved method.

Accordingly, a device for the automated isolation and transfer of at least one microscopic sample from a sample carrier to a collecting system for subsequent automatic analysis is provided, comprising: a selection unit for selecting at least one sample located on the sample carrier; a controllable isolation unit for the automated isolation of the at least one selected sample; a controllable transfer unit, which has carrier means for the defined receiving and deposition of the at least one selected isolated sample, for an automated and defined transfer of the at least one selected isolated sample from the sample carrier to the collecting system; and a control unit, which has a data link to the selection unit, the isolation unit and the transfer unit, for an automated isolation and transfer operation.

A method for the automated isolation and transfer of at least one microscopic sample from a sample carrier to a collecting system is further provided, comprising the following method steps: selecting at least one sample located on the sample carrier by means of a selection unit; automated isolation of the at least one selected sample by means of a controllable isolation unit; automated and defined transfer of the at least one selected isolated sample from the sample carrier to the collecting system by means of a controllable transfer unit, which has carrier means for the defined receiving and deposition of the at least one selected isolated sample; and controlling the isolation unit and the transfer unit by means of a control unit, which has a data link to the selection unit, the isolation unit and the transfer unit, as a function of the step of selecting the at least one sample.

The present invention thus has the advantage over the known approaches that the isolation process and the entire transfer process of the isolated sample(s) from the sample carrier to the collecting system take place in a fully defined and controllable manner. Further, for a high-throughput analysis, all of the method steps may advantageously be synchronised and fully automated. The invention further makes directly subsequent analysis of the deposited sample material possible. Further, damage to the isolated sample as a result of the defined receiving, transfer and deposition is reliably prevented. Further, it is possible to verify the actual transfer process optically.

The dependent claims provide advantageous configurations and improvements of the device and method according to the invention.

In the present document, "defined receiving", "defined deposition" and "defined transfer" of the sample should be understood to mean receiving, deposition and transfer in which the position of the sample at any moment is known in advance and can be influenced, or can at least be detected by the control unit at any moment.

In the present document, a "carrier means" should be understood to be a means which mechanically receives, transfers and deposits the samples, that is to say a positive, material and/or non-positive connection is produced between the sample and the carrier means at least some of the time.

In accordance with a preferred embodiment of the present invention, the selection unit comprises a microscope unit and a display unit coupled thereto, in particular a touchscreen, for displaying the microscopic image of the samples which are available on the sample carrier. Preferably, the display unit comprises selection means for selecting the at least one sample which is to be isolated and transferred, in particular with the aid of optical marking means for graphically identifying on the touchscreen the at least one sample which is to be isolated and transferred. For example, the regions which are to be isolated are marked by way of geometric shapes, and the regions which are marked in this manner are accordingly automatically separated out by means of the isolation unit. A selection of this type and the automated method which starts as a result are advantageously easy to operate. In this way, a user-friendly device and method are advantageously provided.

In accordance with a further preferred embodiment, the isolation unit comprises an appropriately configured laser, in particular a UVA laser, for automated, reproducible isolation of the at least one selected sample without contamination. In this context, the laser is used merely for separating out the selected sample(s) from the carrier as a whole in a defined manner, and not for simultaneously transferring the separated sample onto a corresponding transfer system.

In accordance with a further preferred embodiment, the transfer unit comprises an appropriately configured negative pressure suction system for automated, reproducible transfer of the at least one selected sample which is to be transferred without contamination. Preferably, the transfer unit comprises an autofocus system for adjusting the negative pressure suction system to a precise position at a predetermined distance from the sample which is to be transferred. In this way, the reproducibility and the automation of the transfer method as a whole are further improved. The negative pressure system may for example be configured as disclosed in the European application having application number 08150662.

The negative pressure suction system comprising special carrier means which is preferably used makes possible a defined transport and targeted deposition of for example microdissected samples on for example structured deposits in a droplet of liquid, which is located in particular on a microchip or a microtitre plate. For example, the transfer means comprises specially formed carrier arms and suction means attached thereto, which ensure defined and reproducible transport of the samples. Further, at any moment of the isolation and transfer process as a whole, there is complete control over the individual operational steps and over the respective state of the isolated sample. Further, it is advantageously ensured in a simple manner that homogeneous sample material is obtained for subsequent analysis methods.

In accordance with a further preferred embodiment, the negative pressure suction system comprises a plurality of individually controllable suction units for transferring a plurality of samples simultaneously. As a result, the sample throughput and thus the analysis amount can further be advantageously improved. In this context a magazine system is conceivable, for example, which comprises individual suction units and initially sucks up a predetermined number of samples and subsequently transfers this number of sucked-up samples together to the associated collecting system simultaneously, and again deposits them individually in succession.

In accordance with a further preferred embodiment, the collecting system comprises a portion which is protected in part, in particular a slide shaft which is protected in part, an adapted opening region being provided for depositing the at least one sample on the collecting system by way of the transfer means. In this way, any external contamination is advantageously prevented, and transfer without contamination is ensured.

In accordance with a further advantageous embodiment, a feedback verification unit is provided for confirming successful deposition of the at least one sample on the collecting system, and for example comprises Bragg mirrors in such a way that the reflection thereof is measurably altered after a positive deposition of the at least one sample. In this way, verification of a positive deposition is advantageously ensured, so as to be able to couple in further subsequent biochemical methods automatically in a simple manner. For example, the next, subsequent method is only started after a positive report from the feedback verification unit to confirm the positive deposition.

In accordance with a further advantageous embodiment, the sample is analysed automatically after being deposited successfully on the collecting system, the analysis for example being a biochemical analysis, an optical analysis, a PCR analysis, a nucleic acid analysis (DNA, RNA, siRNA, microRNA) and/or a protein analysis.

The transferred sample can be used for all subsequent methods for qualitative and quantitative nucleic acid and protein diagnostics, such as
1) biochemical methods:
   a. qualitative: gel electrophoresis, PCR, 2D protein gels
   b. quantitative: RT-PCR (real-time polymerase chain reaction)
2) optical methods:
   a. qualitative: fluorescence microscopy, optical density measurement, ELISA, immunohistology methods
   b. quantitative: RT-PCR
3) nucleic acid methods:
   a. qualitative: hybridisation methods (for example FISH, microarray techniques)
   b. quantitative: RT-PCR, cGH (comparative genome analysis, array technologies)

As a result of the miniaturisation and the resulting increased process density, the following diagnostic developments can be pursued:
1) analysis of DNA and proteins to develop new drugs or for the field of personalised medicine
2) miniaturisation of analysis units to the nanoliter range
3) determination of important measurements directly at the hospital bed (point-of-care diagnostics, POC).

BRIEF DESCRIPTION OF THE DRAWINGS

In the following, the invention is described in greater detail by way of embodiments, with reference to the appended drawings, in which.

In the drawings, like reference numerals denote like or functionally equivalent components, unless stated otherwise.

DETAILED DESCRIPTION OF THE INVENTION

Figure 1:
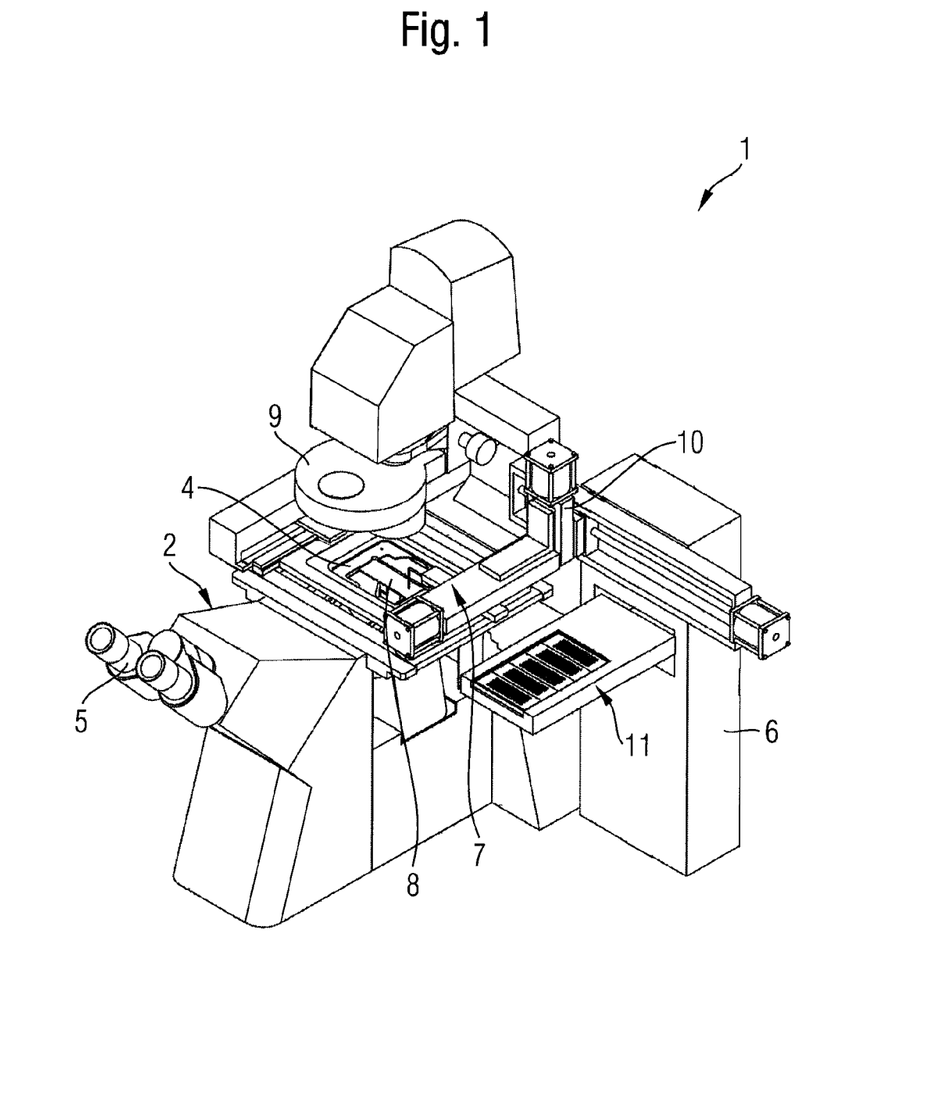
FIG. 1 is a schematic perspective view of a device for the automated isolation and transfer of at least one microscopic sample from a sample carrier to a collecting system in accordance with a preferred embodiment of the present invention, in a sampling position.
Figure 2:
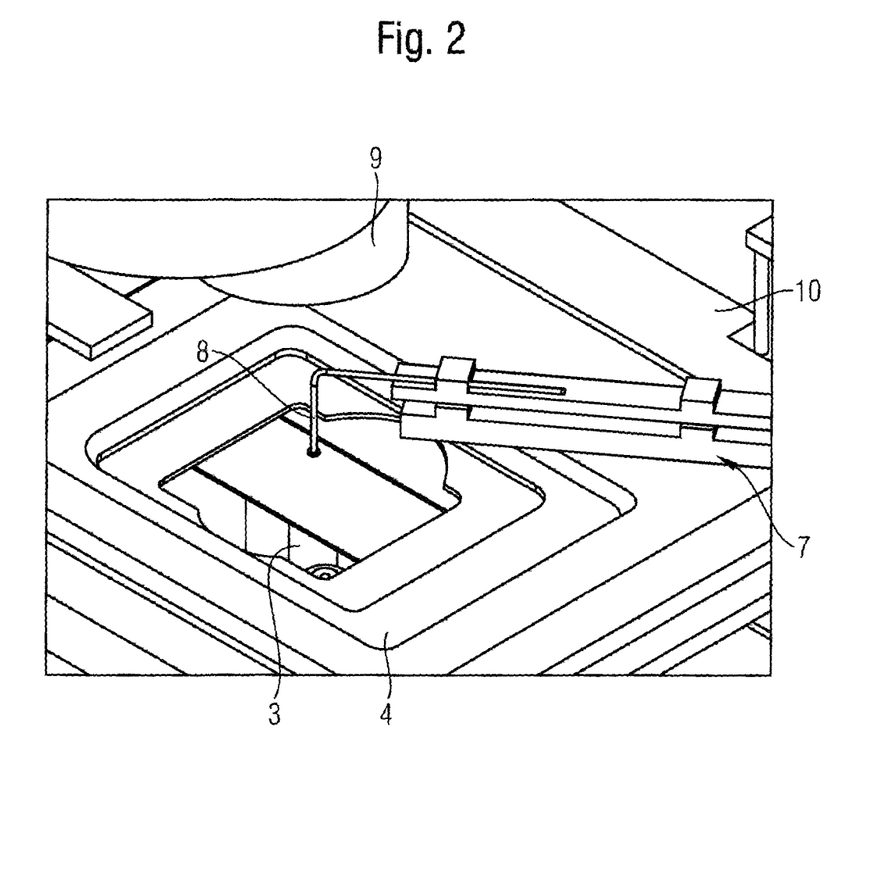
FIG. 2 is an enlarged detail from FIG. 1, showing in particular the microscope unit and the transfer unit.
Figure 3:
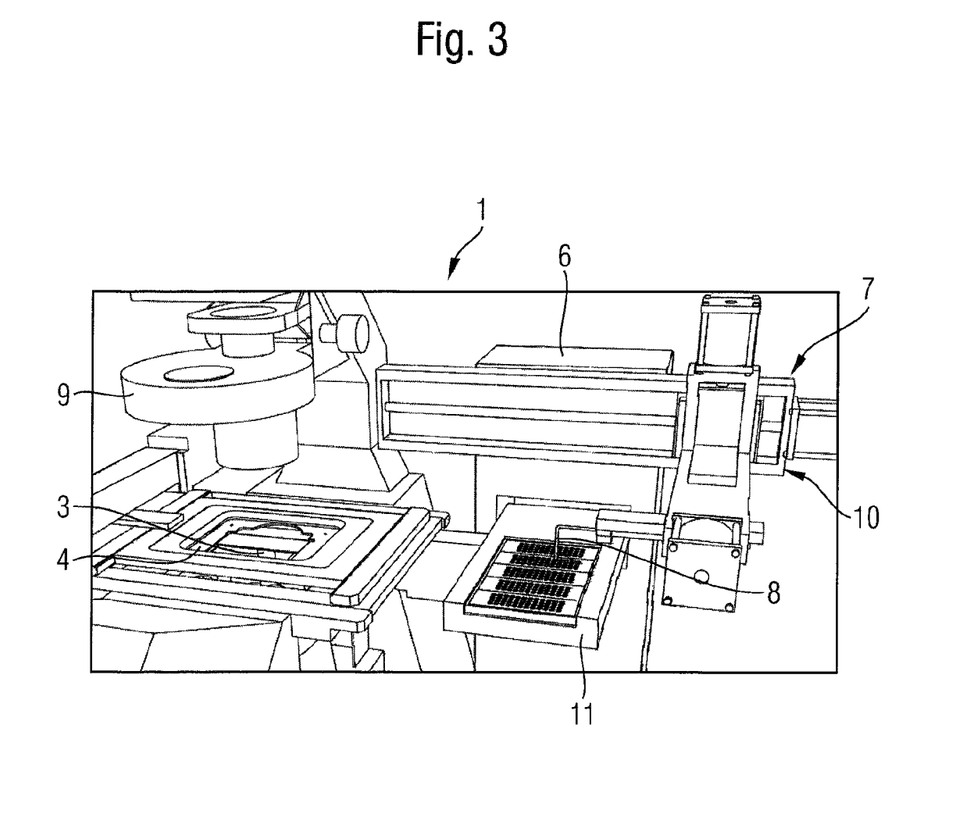
FIG. 3 is a schematic perspective view of the device from FIG. 1, the transfer unit being in the sample deposition position.

In the following, a first preferred embodiment of the present invention is described in greater detail, referring to FIG. 1-3. FIG. 1 is a perspective view of an example device 1 for the automated isolation and transfer of a microscopic sample. This example device 1 comprises a selection unit 2, which comprises as a component in particular a microscope unit 3, in particular in the form of a lens. In accordance with the present embodiment, an object table 4 is formed as a microscope stage, and is provided as a component of the microscope unit. However, the object table 4 may also be formed as an independent microscope stage, in which an object carrier comprising for example a carrier membrane can be gripped. A condenser 9 is further provided, and is arranged between a light source and the microscopic sample which is to be imaged. The condenser 9 deflects the light onto the sample, and the light penetrates said sample and is subsequently incident on the imaging lens, so as to obtain the highest possible resolution.

At this point, it should be noted that this device 1 is formed, by way of example, as a microdissection system for transferring isolated pieces of tissue or cells, referred to in the following as a sample, in particular after laser microdissection. In laser microdissection, the sample is generally arranged on a carrier membrane and is transported from the object table 4 to an analysis unit together with this membrane by a transfer unit, described in greater detail below.

The selection unit 2 preferably further comprises a display unit 5, on which the microscopic image of the samples located on the object table 4 can be visually displayed. For this purpose, the display unit 5 is formed for example as a touchscreen and/or as a telescope-like lens system, as is conventional in microscopes in accordance with FIG. 1, and coupled to the microscope unit 3. By means of corresponding software, in accordance with the present embodiment the user can advantageously mark samples located on the object table 4 for further processing, in particular isolation and transfer, in a simple and user-friendly manner. For example, the samples on the object table 4 which are to be isolated are selected in a targeted manner in that the microscopic image of the samples is imaged on the touchscreen and the regions which are to be isolated of the respective samples are marked on the touchscreen by means of geometric shapes. In this context, it is possible to mark and thus select merely one sample which is to be isolated, or else a plurality of samples which are to be isolated and transferred in succession in accordance with the present embodiment.

In accordance with the present embodiment, the device 1 additionally comprises a controllable isolation unit 6, which is formed for example as a suitable laser, in particular as a UVA laser. By means of the isolation unit 6, the marked and thus selected sample or a predetermined region of the sample body is cut out so as to isolate the sample which is to be transferred. In this context, the isolation unit 6 is preferably coupled to a control unit, which controls in particular the laser focus, the laser energy and the laser triggering as a function of particular specifications.

The device 1 further comprises for example a controllable transfer means 7, which is described in greater detail, for example, in the European patent application having application number 08 150 662. The features of the transfer unit which are disclosed in the European patent application number 08 150 662 are thus also comprised in the present application.

The transfer unit 7 is preferably formed so as to be autonomous and integrable into existing systems, in the present case integrable into the device 1 in such a way that the transfer unit 7 can be attached rigidly to the microscope unit 3. The transfer unit comprises for example a suction unit 8 which is used for sucking up the sample from the object table 4, in the sampling position which is shown in FIG. 1 and in an enlarged view in FIG. 2, or for blowing out the sample in the sample deposition position which is shown in FIG. 3.

The suction unit 8 comprises for example a nanosucker, which consists for example of a borosilicate glass tube and an end membrane. In accordance with the present embodiment, the glass tube is of an L shape and the end thereof is connected to a coupling tube in an airtight manner. The other end of the glass tube comprises an end membrane, comprising a carrier plate and an end grating, at the end face. The carrier plate is for example formed as a disc having a central hole. The carrier plate preferably consists of an electrically conductive material, such as copper or the like. The carrier plate is preferably fixed to the end face of the head portion of the nanosucker in such a way that a central hole of the carrier plate is flush with the opening of the suction tube.

The end membrane further comprises an end grating, which is likewise preferably formed from an electrically conductive material or a material having an electrically conductive surface. The end grating is for example also in the form of a round disc, the grating thickness and the pore size of the end grating preferably being adaptable in an appropriate manner to the respective sample which is to be transferred. For example, a grid thickness of approximately 20 µm and pores having a diameter of between approximately 60 nm and 50 µm are conceivable. The end grating is preferably attached to the carrier plate in such a way that the grating fully overlaps the hole of the carrier plate and thus the opening of the suction tube. The entire arrangement is preferably formed in such a way that the suction air is passed directly through the grating, and not to the environment at any leaky points.

Electrostatic charging of the nanosucker should be prevented so as to protect the sample. Electrical contact points are therefore provided for an electrical connection between the carrier plate and the electrically conductive coating of the suction tube. In this way, electrostatic charges which are induced for example by particular samples or the material of the end membrane can advantageously be dissipated via the suction tube or an earth line associated with the suction tube.

Furthermore, the transfer unit 7 further comprises a negative pressure/overpressure unit, for example a pneumatic pico pump, which provides the desired negative pressure for sucking up the sample onto the end grating or the respectively desired overpressure for blowing the sample out of the end grating onto the collecting system 11. For this purpose, the negative pressure/overpressure unit is coupled to the suction unit 8 in a suitable manner. The negative pressure/overpressure unit further has a data link to the control unit, in such a way that a corresponding setting, adapted to the respective application, of the negative pressure/overpressure unit is ensured. In particular, in this way the suction power or the strength of the blowing pulse of the negative pressure/overpressure unit can preferably be set and controlled in advance in accordance with the respective application. It is also advantageous to be able to regulate the overpressure duration of a few ms, so as to be able to pass the received sample reliably into a provided droplet of liquid on an analysis unit, which is to be explained in greater detail in the following, or on the collecting system 11, without breaking up this droplet.

The transfer means 7 preferably further comprises an autofocus system, which is also coupled to the control unit and controls the approach of the negative pressure system at a defined distance from the sample surface. For example, a suitable laser sensor is provided, and measures online the distance between the end membrane and the sample which is to be received or the distance from the collecting system 11 on which the received sample is to be deposited. For example, an LTA-02 laser sensor autofocus unit for automatic distance regulation can be used as the laser sensor, and automatically sets a target distance of for example 100 μm between the relevant surfaces.

The transfer unit 7 further comprises a carrier unit 10, on which at least the suction unit 8 is arranged. The carrier unit 10 is preferably coupled to an associated positioning unit. Preferably, for adjusting the carrier means 10, four degrees of freedom of the positioning unit are provided, three translational movements and a rotational movement for pivoting the carrier means in the horizontal plane. Preferably, vibration-damped stepper motors are used for precisely positioning the suction unit 8. However, it is obvious to a person skilled in the art that other drives which are similarly appropriate may also be used in this context. For example, a micrometer stepper motor, which can position the carrier unit 10 and thus the nanosucker to a precision in the μm range, is used.

In the case where the transfer unit 7 is attached to an associated microscope unit 3, the object table 4 merely has to be adjusted accordingly, exact positioning of the nanosucker being ensured by way of the lens system or laser system of the microscope unit 3 when the carrier means 10 pivots, since the carrier means 10 is adjusted in the reference system of the microscope unit 3 as a result of the rigid attachment. In this way, maximum precision and rapid reception of the respective samples, including relatively small samples, is ensured. The entire adjustment movement is carried out in an automated manner by way of corresponding software and the aforementioned central control unit.

The device 1 further comprises a collecting system 11, which is preferably accommodated in a protected slide shaft and is used as a deposit station for the individual samples. The collecting system consists for example of a structured receiving carrier comprising individual deposition points under an appropriate cover, merely a predetermined opening range being ensured so as to receive the corresponding sample or samples through the transfer unit 7. Only a small region is accessible to the transfer unit 7, so as to prevent any external contamination of the sample(s) which are to be transferred and analysed. The collecting system 11 too can preferably be attached to a predetermined microscope unit 3 by way of a corresponding adapter.

The individual components, or at least a particular selection of the aforementioned components, preferably have a data link to the central control unit, in such a way that the entire isolation and transfer and deposition process can run in a fully automated manner on a structured collecting system by means of the central control unit, by selecting the sample(s) which are to be isolated and transferred. Further, as a result of the above-disclosed device 1, a defined isolation and transfer without contamination are ensured. All of the process steps by means of the aforementioned device 1 run in a synchronised and fully automated manner, in such a way that high-throughput analysis is ensured. The negative pressure suction system makes it possible to receive the isolated samples from the sample carrier without contact and to deposit them in a targeted manner in extremely small volumes, for example 50 to 400 nl, preferably at most 1000 nl, on any type of structured collecting system. For example, the collecting system may be a multititre plate, a functionalised glass object carrier or a biochip (lab on a chip system). In this context, the samples can be received individually or in a pooled manner. For this purpose, the negative pressure which is applied to the transfer means 7 is upheld, it being possible to use one or more suckers as the suction unit 8 for the sampling. In this context, these suckers may be controlled individually or together by means of the central control unit. The isolated sample or samples are deposited above the predetermined deposition location in a targeted manner in a small droplet of liquid for further analysis.

The further analysis comprises for example a biochemical analysis, an optical analysis, a PCR analysis, a nucleic acid analysis and/or a protein analysis.

The device 1 may also comprise further components besides those stated above, for example a feedback verification unit (not shown) which provides the user, in a simple manner, with verification as to whether or not a sample has been deposited in the collecting system as desired. The feedback verification unit comprises Bragg mirrors, for example. These Bragg mirrors may be considered as a grating, and measurably change the reflection thereof in the case of a positive deposition of a sample, in such a way that a positive feedback system can be provided so as to confirm positive deposition. This is advantageous because further subsequent biochemical processes can only be carried out if a positive deposition has occurred beforehand.

The control preferably takes place by way of specially developed software and makes possible, among other things, the necessary regulation of the overpressure duration of a few ms and the pivoting movement of the transfer unit, so as to be able to deposit the received sample reliably in for example a predetermined droplet of liquid of the collecting system 11, without breaking it up. All of the parameters which are necessary for the control can be set freely by way of the software.

Figure 4:
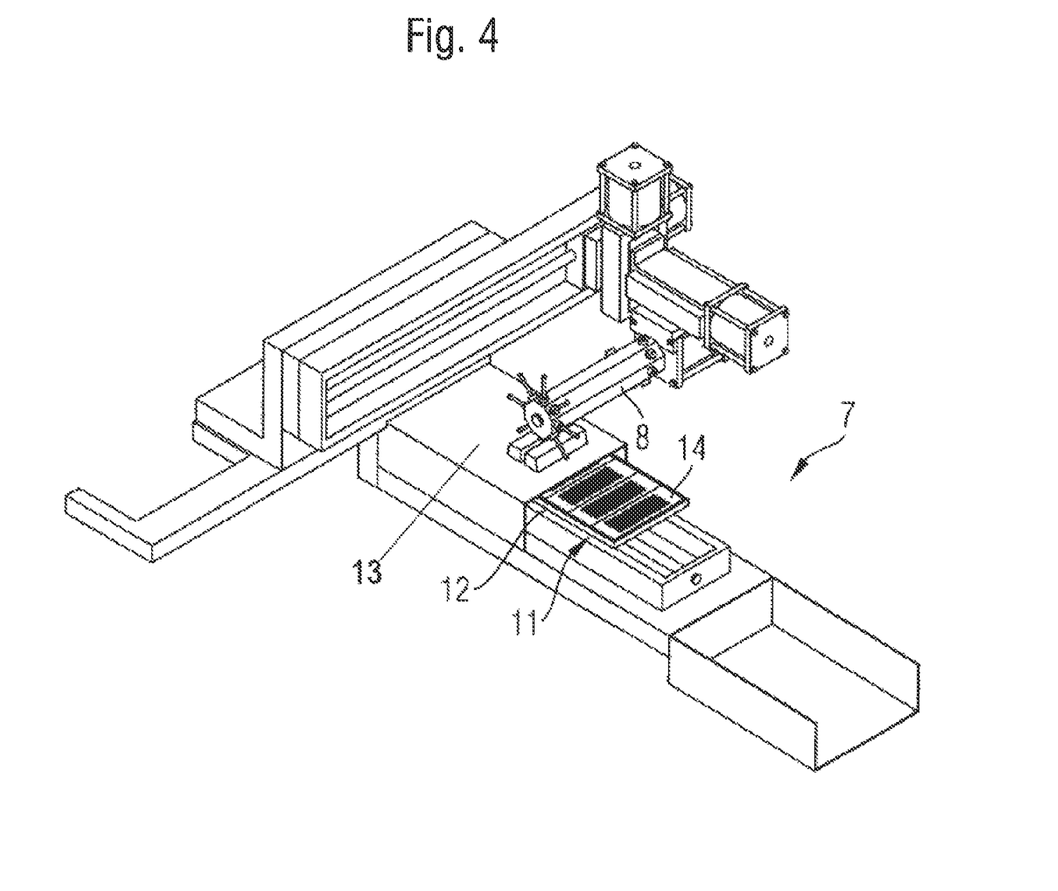
FIG. 4 is a schematic perspective view of a transfer unit and a collecting system in accordance with a further preferred embodiment of the present invention.
Figure 5:
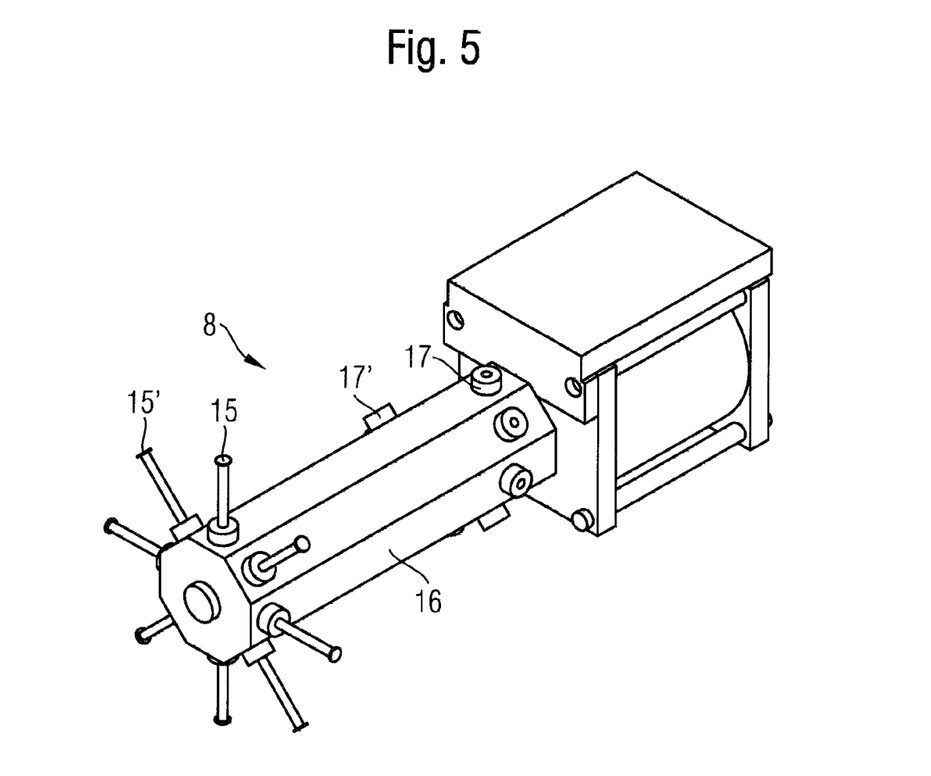
FIG. 5 is a perspective view of the suction unit of the transfer unit in accordance with the preferred embodiment from FIG. 4.

A transfer unit 7 in accordance with a second preferred embodiment of the present invention is shown in FIGS. 4 and 5 and explained in greater detail in the following. As regards components, configurations and modes of operation of the individual components which are not described in greater detail in the following, reference is made to the embodiment described above.

Initially, it can be seen from FIG. 4 that the collecting system 11 consists of an exposable slide shaft 12 and a foldable cover 13. The individual regions of the deposition plate 14 can be retracted and extended in and out of a protected shaft region by way of the slide system. This serves to prevent any external contamination of the deposited samples. The collecting system shown in FIG. 4 is of course also transferable to the first embodiment in accordance with FIG. 1-3.

Further, FIG. 5 is an enlarged drawing of the suction unit 8 in accordance with the second preferred embodiment from FIG. 4. This suction unit 8 is used to receive a plurality of samples, in accordance with the present embodiment at most eight, by means of individual suckers 15, 15'.

The suction unit 8 in accordance with the embodiment of FIG. 5 comprises for example a rotatable cylinder or revolver 16, the individual suckers 15, 15' having individual suction tubes and these suction tubes in turn being controllable individually via respective pressure lines. The individual pressure lines are accordingly attached in an airtight manner to the terminals 17, 17' associated with the respective suckers 15, 15' and controlled accordingly by means of the central control unit. This makes possible individual suction or deposition of the respective isolated samples. The individual connections of the pressure lines to the terminals 17, 17' take place for example by means of an "easy to click" system, in such a way that the respective number of suckers to be used can be selected freely in a simple manner. In the case where merely one sucker 15 is used, no rotation of the cylinder or revolver 16 is necessary. If a plurality of suckers 15, 15' are used, additional pressure lines are applied to the corresponding terminals 17, 17', the cylinder or revolver 16 is rotated accordingly, and the individual isolated samples are received in succession. Further, in accordance with the present embodiment, a simple exchange of the individual suckers 15, 15' is ensured, and this leads to a process without contamination.

In this context, the suction unit 8 or the individual suckers 15 may be selected individually and controlled by the control unit in such a way that a particular sucker 15 is displaced over the object table 4 by rotating the cylinder 16 of the suction unit 8, and receives an isolated sample. Once this sample has been received by this sucker 15, the cylinder 16 of the suction unit 8 is rotated through a predetermined angle in such a way that a further predetermined sucker 15' is positioned above the object table 4 for receiving a further, already isolated sample. In accordance with the number and sequence of the initially selected samples which are to be isolated and transferred, this step is repeated in succession, at most until all of the suckers 15, 15' have received a corresponding isolated sample. Subsequently, the suction unit 8 is adjusted by means of the transfer means 7 with respect to the collecting system 11 by means of the provided stepper motors. The individual suckers 15, 15' are subsequently positioned over the corresponding deposition points of the deposition plate 14 of the collecting system 11 in succession by means of the control unit, and the samples adhering thereto are accordingly deposited, the cylinder or revolver 16 being rotated again accordingly after depositing a sample in such a way that a further sample can be deposited in an appropriate manner by means of the negative pressure/overpressure system.

The present invention thus provides a device and a method for the automated isolation and transfer of at least one microscopic sample or a plurality thereof from a sample carrier to a collecting system by means of carrier means. Advantageously, the horizontal transport and a targeted deposition of microdissected samples on structured deposits in a droplet of liquid are made possible. In this context, the microdissected samples are isolated and transported in a fully automated manner, and there is complete control over the individual operational steps and the state of the respectively isolated sample(s) at every moment in the process. Further, the device described above can be operated in a simple manner, since it is merely necessary to select the samples to be analysed by way of the touchscreen.

Although the present invention has been described by way of preferred embodiments, it is not limited thereto, but can be modified in a variety of ways. In particular, the suction unit can also be configured in a different manner from that described above, as long as a fully automated receiving and deposition of one or more samples is ensured. Further, for example, the collecting system or the deposition plate integrated into it can be scaled as desired because of the high accuracy and precision of the transfer unit. In this way, both microtitre plates and microchips comprising nanoliter droplets can advantageously be controlled.

The invention claimed is:

1. A device for selection and the automated isolation and transfer of at least one microscopic sample from a sample carrier to a collecting system for subsequent automatic analysis, comprising:
    a selection unit by which at least one sample located on the sample carrier can be selected by a user;
    a controllable isolation unit for the automated isolation of the at least one selected sample;
    a controllable transfer unit, which has carrier means for the defined receiving and defined deposition of the at least one selected isolated sample, for the automated and defined transfer of the at least one selected isolated sample from the sample carrier to the collecting system; and
    a control unit, which has a data link to the selection unit, the isolation unit and the transfer unit, for an automated isolation and transfer operation,
    wherein the transfer unit comprises a negative pressure suction system that transfers the at least one sample without contamination.

2. The device according to claim 1, wherein the selection unit comprises a microscope unit and a display unit coupled thereto for displaying the microscopic image of the samples which are available on the sample carrier.

3. The device according to claim 2, wherein the display unit is configured as a touchscreen.

4. The device according to claim 3, wherein the display unit comprises selection means by which the at least one sample which is to be isolated and transferred can be selected by the user with the aid of optical marking means for graphically identifying on the touchscreen the at least one sample which is to be isolated and transferred.

5. The device according to claim 2, wherein the display unit comprises selection means by which the at least one sample which is to be isolated and transferred can be selected by a user.

6. The device according to claim 1, wherein the isolation unit comprises an appropriately configured laser for the automated isolation of the at least one selected sample without contamination.

7. The device according to claim 6, wherein the laser is configured as a UVA laser.

8. The device according to claim 1, wherein the transfer unit comprises an autofocus system for adjusting the negative pressure suction system to a precise position at a predetermined distance from the at least one sample which is to be transferred.

9. The device according to claim 1, wherein the negative pressure suction system comprises a plurality of individually controllable suction units for transferring a plurality of samples simultaneously.

10. The device according to claim 1, wherein the collecting system comprises a portion which is protected in part, an adapted opening region being provided for depositing the at least one sample on the collecting system by way of the transfer unit.

11. The device according to claim 10, wherein the portion which is protected in part is configured as a slide shaft which is protected in part.

12. The device according to claim 1, wherein a feedback verification unit is further provided for confirming successful deposition of the at least one sample on the collecting system.

13. The device according to claim 12, wherein the feedback verification unit comprises Bragg mirrors in such a way that the reflection thereof is measurably altered after a positive deposition of the at least one sample.

14. A method for selection and for the automated isolation and transfer of at least one microscopic sample from a sample carrier to a collecting system, comprising the following method steps:
    selecting at least one sample located on the sample carrier by a user by means of a selection unit;
    automated isolation of the at least one selected sample by means of a controllable isolation unit;
    automated and defined transfer of the at least one selected isolated sample from the sample carrier to the collecting system by means of a controllable transfer unit, which has carrier means for the defined receiving and defined deposition of the at least one selected isolated sample; and
controlling the isolation unit and the transfer unit by means of a control unit, which has a data link to the selection unit, the isolation unit and the transfer unit, as a function of the step of selecting the at least one sample,
wherein the at least one sample which is to be transferred is transferred in an automated and defined manner, without contamination, by a negative pressure suction system.

15. The method according to claim 14, wherein a microscopic image of the samples which are available on the sample carrier is displayed by means of a microscope unit and a display unit coupled thereto.

16. The method according to claim 15, wherein display unit is configured as a touchscreen.

17. The method according to claim 16, wherein the at least one sample which is to be isolated and transferred is selected by the user by means of optical marking means for graphically identifying on the touchscreen the at least one sample which is to be isolated and transferred.

18. The method according to claim 15, wherein the at least one sample which is to be isolated and transferred is selected by a user by means of selection means.

19. The method according to claim 14, wherein the at least one selected sample is isolated in an automated and defined manner, without contamination, by means of an appropriately configured laser.

20. The method according to claim 19, wherein the at least one selected sample is isolated by means of a UVA laser.

21. The method according to claim 14, wherein the negative pressure system is adjusted by means of an autofocus system so as to be set in a precise position at a predetermined distance from the at least one sample which is to be transferred.

22. The method according to claim 14, wherein the negative pressure suction system is formed with a plurality of individually controllable suction means for simultaneously transferring a plurality of samples.

23. The method according to claim 14, wherein the collecting system is formed with a portion which is protected at least in part, an adapted opening region being provided for depositing the at least one sample on the collecting system by way of the transfer means.

24. The method according to claim 23, wherein the collecting system is formed with a slide shaft which is protected at least in part.

25. The method according to claim 14, wherein successful deposition of the at least one sample on the collecting system is carried out by means of a feedback verification unit.

26. The method according to claim 25, wherein the feedback verification unit comprises Bragg mirrors in such a way that the reflection thereof is measurably altered after positive deposition of the at least one sample.

27. The method according to claim 14, wherein the sample is analyzed automatically after being deposited successfully on the collecting system.

28. The method according to claim 27, wherein the analysis is at least one of a biochemical analysis, an optical analysis, a PCR analysis, a nucleic acid analysis, a protein analysis.

* * * * *